US009878285B2

(12) United States Patent
Schraven et al.

(10) Patent No.: US 9,878,285 B2
(45) Date of Patent: Jan. 30, 2018

(54) METHOD AND ABSORPTION MEDIUM FOR ABSORBING $CO_2$ FROM A GAS MIXTURE

(71) Applicant: Evonik Industries AG, Essen (DE)

(72) Inventors: Alexander Schraven, Issum (DE); Günter Knaup, Bruchköbel (DE); Rolf Schneider, Gründau-Rothenbergen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/373,350

(22) PCT Filed: Nov. 28, 2012

(86) PCT No.: PCT/EP2012/073778
§ 371 (c)(1),
(2) Date: Jul. 19, 2014

(87) PCT Pub. No.: WO2013/110374
PCT Pub. Date: Aug. 1, 2013

(65) Prior Publication Data
US 2014/0356268 A1 Dec. 4, 2014

(30) Foreign Application Priority Data
Jan. 23, 2012 (DE) .................. 10 2012 200 907

(51) Int. Cl.
B01D 53/62 (2006.01)
B01D 53/14 (2006.01)
C07C 229/06 (2006.01)
C07C 229/08 (2006.01)
C07C 229/10 (2006.01)
C07C 229/12 (2006.01)
C07C 227/18 (2006.01)

(52) U.S. Cl.
CPC ......... B01D 53/62 (2013.01); B01D 53/1475 (2013.01); B01D 53/1493 (2013.01); C07C 227/18 (2013.01); C07C 229/06 (2013.01); B01D 2252/20494 (2013.01); B01D 2258/025 (2013.01); B01D 2258/0233 (2013.01); B01D 2258/0283 (2013.01); B01D 2258/05 (2013.01); Y02C 10/06 (2013.01); Y02P 20/152 (2015.11)

(58) Field of Classification Search
None
See application file for complete search history.

(56) References Cited

U.S. PATENT DOCUMENTS

| 1,882,258 | A | 10/1932 | Randel |
|---|---|---|---|
| 2,516,625 | A | 7/1950 | Haury |
| 2,601,673 | A | 6/1952 | McMillan et al. |
| 2,802,344 | A | 8/1957 | Witherell |
| 3,137,654 | A | 6/1964 | Johnson et al. |
| 3,276,217 | A | 10/1966 | Bourne et al. |
| 3,580,759 | A | 5/1971 | Albertson et al. |
| 3,609,087 | A | 9/1971 | Chi et al. |
| 4,079,263 | A | 3/1978 | Inoue |
| 4,094,957 | A | 6/1978 | Sartori et al. |
| 4,106,904 | A | 8/1978 | Oude Alink et al. |
| 4,112,051 | A | 9/1978 | Sartori et al. |
| 4,152,900 | A | 5/1979 | Chopra et al. |
| 4,152,901 | A | 5/1979 | Munters |
| 4,201,721 | A | 5/1980 | Hallgren |
| 4,217,238 | A | 8/1980 | Sartori et al. |
| 4,251,494 | A | 2/1981 | Say |
| 4,360,363 | A | 11/1982 | Ferrin et al. |
| 4,405,579 | A | 9/1983 | Sartori et al. |
| 4,405,586 | A | 9/1983 | Sartori et al. |
| 4,466,915 | A | 8/1984 | Lai |
| 4,489,563 | A | 12/1984 | Kalina |
| 4,524,587 | A | 6/1985 | Kantor |
| 4,525,294 | A | 6/1985 | Sartori et al. |
| 4,605,743 | A | 8/1986 | Malz et al. |
| 4,643,000 | A | 2/1987 | Rheinfelder |
| 4,701,530 | A | 10/1987 | Swearingen et al. |
| 4,714,597 | A | 12/1987 | Trevino |
| 4,889,938 | A | 12/1989 | Kristen et al. |
| 5,016,445 | A | 5/1991 | Wehr |
| 5,126,189 | A | 6/1992 | Tanny et al. |
| 5,186,009 | A | 2/1993 | Rockenfeller |
| 5,186,010 | A | 2/1993 | Wehr |

(Continued)

FOREIGN PATENT DOCUMENTS

| CA | 2 817 704 | 5/2012 |
|---|---|---|
| CN | 1076380 A | 9/1993 |

(Continued)

OTHER PUBLICATIONS

English translation of the International Search Report for corresponding international application PCT/EP2012/073778 filed Nov. 28, 2012.
English language translation of the Written Opinion of the International Searching Authority for corresponding application PCT/EP2012/073778 filed Nov. 28, 2012.
English language translation of the International Preliminary Report on Patentability for corresponding international application PCT/EP2012/073778 filed Nov. 28, 2012.
Brennecke, et al., "Ionic Liquids: Innovative Fluids for Chemical Processing," *AIChE Journal* 47(11):2384-2389 (Nov. 2001).
Chua, et al., "Improved Thermodynamic Property Fields of LiBr-$H_2O$ Solution," *International Journal of Refrigeration* 23:412-429 (Sep. 2000).

(Continued)

Primary Examiner — Daniel Berns
(74) Attorney, Agent, or Firm — Law Office of: Michael A. Sanzo, LLC

(57) ABSTRACT

The absorption of $CO_2$ from a gas mixture by contacting the gas mixture with an absorption medium that comprises water and 5 to 50 wt % of amino acid salts of formula $R^1R^2CHNHCH_2COOK$, in which $R^1$ and $R^2$ are n-alkyl radicals and the radicals $R^1$ and $R^2$ together have 2 to 4 carbon atoms, affords a high $CO_2$ absorption capacity per unit weight in the cyclical operation of absorption and desorption.

19 Claims, No Drawings

(56) References Cited

U.S. PATENT DOCUMENTS

| | | |
|---|---|---|
| 5,255,534 A | 10/1993 | Ryan |
| 5,303,565 A | 4/1994 | Pravda |
| 5,390,509 A | 2/1995 | Rockenfeller et al. |
| 5,873,260 A | 2/1999 | Linhardt et al. |
| 6,117,963 A | 9/2000 | Boinowitz et al. |
| 6,128,917 A | 10/2000 | Riesch et al. |
| 6,130,347 A | 10/2000 | Julius et al. |
| 6,155,057 A | 12/2000 | Angell et al. |
| 6,165,433 A | 12/2000 | Chakravarti et al. |
| 6,184,433 B1 | 2/2001 | Harada et al. |
| 6,423,282 B1 | 7/2002 | Araki et al. |
| 6,475,370 B2 | 11/2002 | Lehmann et al. |
| 6,672,099 B1 | 1/2004 | Yoshimi et al. |
| 6,680,047 B2 | 1/2004 | Klaveness et al. |
| 6,727,015 B1 | 4/2004 | Putter et al. |
| 7,419,646 B2 | 9/2008 | Cadours et al. |
| 7,435,318 B2 | 10/2008 | Arlt et al. |
| 7,638,636 B2 | 12/2009 | Zhou et al. |
| 7,666,813 B2 | 2/2010 | Hoefer et al. |
| 7,754,053 B2 | 7/2010 | Maase |
| 7,827,820 B2 | 11/2010 | Weimer et al. |
| 7,998,714 B2 | 8/2011 | Gellett et al. |
| 8,069,687 B2 | 12/2011 | Jork et al. |
| 8,167,983 B2 | 5/2012 | Seiler et al. |
| 8,277,615 B2 | 10/2012 | Ruffert et al. |
| 8,318,117 B2 | 11/2012 | Lichtfers et al. |
| 8,357,344 B2 | 1/2013 | Bouillon et al. |
| 8,362,095 B2 | 1/2013 | Schwab et al. |
| 8,382,962 B2 | 2/2013 | Massonne et al. |
| 8,470,079 B2 | 6/2013 | Agar et al. |
| 8,500,867 B2 | 8/2013 | Seiler et al. |
| 8,500,892 B2 | 8/2013 | Seiler et al. |
| 8,506,839 B2 | 8/2013 | Shiflett et al. |
| 8,523,978 B2 | 9/2013 | Rojey et al. |
| 8,623,123 B2 | 1/2014 | Seiler et al. |
| 8,696,928 B2 | 4/2014 | Seiler et al. |
| 8,703,451 B2 | 4/2014 | Haas et al. |
| 8,715,521 B2 | 5/2014 | Shiflett et al. |
| 8,784,537 B2 | 7/2014 | Seiler et al. |
| 8,809,576 B2 | 8/2014 | Schraven et al. |
| 8,932,478 B2 | 1/2015 | Seiler et al. |
| 9,221,007 B2 | 12/2015 | Rolker et al. |
| 2004/0016631 A1 | 1/2004 | Madkour |
| 2004/0133058 A1 | 7/2004 | Arlt et al. |
| 2005/0070717 A1 | 3/2005 | Wasserscheid et al. |
| 2005/0129598 A1 | 6/2005 | Chinn |
| 2005/0164082 A1 | 7/2005 | Kishi et al. |
| 2005/0202967 A1 | 9/2005 | Hoefer et al. |
| 2005/0245769 A1 | 11/2005 | Kohler et al. |
| 2006/0104877 A1 | 5/2006 | Cadours et al. |
| 2006/0150665 A1 | 7/2006 | Weimer et al. |
| 2006/0197053 A1 | 9/2006 | Shiflett et al. |
| 2006/0251961 A1 | 11/2006 | Olbert et al. |
| 2007/0004903 A1 | 1/2007 | Hoff et al. |
| 2007/0095645 A1 | 5/2007 | Masse |
| 2007/0144186 A1 | 6/2007 | Shiflett et al. |
| 2007/0264180 A1 | 11/2007 | Carrette et al. |
| 2007/0286783 A1 | 12/2007 | Carrette et al. |
| 2008/0028777 A1 | 2/2008 | Boesmann et al. |
| 2008/0114105 A1 | 5/2008 | Hell et al. |
| 2008/0283383 A1 | 11/2008 | Ruffert et al. |
| 2009/0029121 A1 | 1/2009 | Hammermann et al. |
| 2009/0029887 A1 | 1/2009 | Schwab et al. |
| 2009/0036334 A1 | 2/2009 | Schwab et al. |
| 2009/0139232 A1 | 6/2009 | Collis |
| 2009/0170734 A1 | 7/2009 | Schwab et al. |
| 2009/0199709 A1 | 8/2009 | Rojey et al. |
| 2009/0211447 A1 | 8/2009 | Lichtfers et al. |
| 2010/0011958 A1 | 1/2010 | Cadours et al. |
| 2010/0016205 A1 | 1/2010 | Schwab |
| 2010/0029519 A1 | 2/2010 | Schwab et al. |
| 2010/0071557 A1 | 3/2010 | Seiler et al. |
| 2010/0084597 A1 | 4/2010 | Schwab et al. |
| 2010/0086983 A1 | 4/2010 | Gellett et al. |
| 2010/0095703 A1 | 4/2010 | Jork et al. |
| 2010/0104490 A1 | 4/2010 | Bouillon et al. |
| 2010/0132551 A1 | 6/2010 | Bouillon et al. |
| 2010/0186590 A1 | 7/2010 | Vorberg et al. |
| 2010/0288126 A1 | 11/2010 | Agar et al. |
| 2010/0300870 A1 | 12/2010 | Massonne et al. |
| 2010/0326126 A1 | 12/2010 | Seiler et al. |
| 2011/0000236 A1 | 1/2011 | Seiler et al. |
| 2011/0081287 A1 | 4/2011 | Bouillon et al. |
| 2011/0094381 A1 | 4/2011 | Lichtfers et al. |
| 2011/0118504 A1 | 5/2011 | Haas et al. |
| 2011/0135549 A1 | 6/2011 | Lichtfers et al. |
| 2011/0185901 A1 | 8/2011 | Jacquin et al. |
| 2011/0247494 A1 | 10/2011 | Dinnage et al. |
| 2011/0256043 A1 | 10/2011 | Blair et al. |
| 2011/0309295 A1 | 12/2011 | Joh et al. |
| 2012/0011886 A1 | 1/2012 | Shiflett et al. |
| 2012/0017762 A1 | 1/2012 | Seiler et al. |
| 2012/0080644 A1 | 4/2012 | Seiler et al. |
| 2012/0117991 A1 | 5/2012 | Rached |
| 2012/0247144 A1 | 10/2012 | Seiler et al. |
| 2012/0308458 A1 | 12/2012 | Seiler et al. |
| 2012/0315366 A1 | 12/2012 | Zehnacher et al. |
| 2013/0011314 A1 | 1/2013 | Porcheron et al. |
| 2013/0023712 A1 | 1/2013 | Porcheron et al. |
| 2013/0031930 A1 | 2/2013 | Seiler et al. |
| 2013/0031931 A1 | 2/2013 | Seiler et al. |
| 2013/0118350 A1 | 5/2013 | Rolker et al. |
| 2013/0133327 A1 | 5/2013 | Milam et al. |
| 2013/0219949 A1 | 8/2013 | Seiler et al. |
| 2013/0247758 A1 | 9/2013 | Seiler et al. |
| 2013/0263743 A1 | 10/2013 | Seiler et al. |
| 2013/0327084 A1 | 12/2013 | Shiflett et al. |
| 2014/0005344 A1 | 1/2014 | Rinker et al. |
| 2014/0090558 A1 | 4/2014 | Rolker et al. |
| 2014/0105801 A1 | 4/2014 | Rolker et al. |
| 2014/0120016 A1 | 5/2014 | Rolker et al. |
| 2014/0360369 A1 | 12/2014 | Schraven et al. |
| 2015/0024106 A1 | 1/2015 | Huller et al. |
| 2015/0024247 A1 | 1/2015 | Lockett et al. |
| 2015/0125373 A1 | 5/2015 | Willy et al. |
| 2015/0175738 A1 | 6/2015 | Willy et al. |
| 2015/0175740 A1 | 6/2015 | Willy et al. |
| 2015/0308720 A1 | 10/2015 | Zehnacker et al. |
| 2015/0321139 A1 | 11/2015 | Schraven et al. |
| 2016/0045857 A1 | 2/2016 | Rolker et al. |
| 2016/0115827 A1 | 4/2016 | Rached |
| 2016/0153318 A1 | 6/2016 | Busse et al. |
| 2016/0175766 A1 | 6/2016 | Zehnacker |

FOREIGN PATENT DOCUMENTS

| | | |
|---|---|---|
| CN | 102335545 | 2/2012 |
| DE | 400 488 | 8/1924 |
| DE | 633 146 | 7/1936 |
| DE | 737031 | 7/1943 |
| DE | 36 23 680 A1 | 1/1988 |
| DE | 266 799 A1 | 4/1989 |
| DE | 195 11 709 | 10/1996 |
| DE | 103 33 546 | 2/2005 |
| DE | 10 2004 053 167 | 5/2006 |
| DE | 10 2010 001 0 | 7/2011 |
| DE | 10 2010 004 779 | 7/2011 |
| DE | 10 2011 055 859 | 6/2013 |
| DE | 10 2013 010 0 | 12/2014 |
| DE | 10 2014 214 6 | 1/2016 |
| DE | 10 2015 212 7 | 1/2017 |
| DE | 10 2016 210 4 | 6/2017 |
| EP | 0 033 529 A1 | 1/1981 |
| EP | 0 047 967 | 9/1981 |
| EP | 0 079 767 | 5/1983 |
| EP | 0 187 130 | 7/1986 |
| EP | 0 193 327 | 9/1986 |
| EP | 0 302 020 | 2/1989 |
| EP | 0 558 019 | 2/1993 |
| EP | 2 636 715 | 9/2013 |
| FR | 670 497 | 11/1929 |
| FR | 2 900 841 A1 | 11/2007 |
| GB | 1 306 853 | 2/1973 |
| GB | 1 501 195 | 2/1978 |

(56) References Cited

FOREIGN PATENT DOCUMENTS

| | | |
|---|---|---|
| GB | 2 047 681 | 12/1980 |
| GB | 2 528 494 | 1/2016 |
| JP | 33-009879 B | 11/1958 |
| JP | 57-191407 | 11/1982 |
| JP | 61-129019 | 6/1986 |
| JP | 62-73055 | 4/1987 |
| JP | 1-134180 | 5/1989 |
| JP | 2-298767 | 12/1990 |
| JP | 4-268176 | 9/1992 |
| JP | 6-307730 | 11/1994 |
| JP | 7-167521 | 7/1995 |
| JP | 2001-219164 | 8/2001 |
| JP | 2002-047258 | 2/2002 |
| JP | 2004-44945 | 2/2004 |
| JP | 2006-239516 | 9/2006 |
| JP | 2006-282525 | 10/2006 |
| JP | 2013-051238 | 3/2013 |
| RU | 2 101 625 | 1/1998 |
| RU | 2 122 642 | 11/1998 |
| RU | 2 183 003 | 5/2002 |
| WO | WO 93/13367 | 7/1993 |
| WO | WO 00/61698 A1 | 10/2000 |
| WO | WO 02/16671 | 2/2002 |
| WO | WO 2004/016631 | 2/2004 |
| WO | WO 2004/082809 | 9/2004 |
| WO | WO 2006/012097 | 2/2006 |
| WO | WO 2006/048182 | 5/2006 |
| WO | WO 2007/099041 | 9/2007 |
| WO | WO 2009/074535 | 6/2009 |
| WO | WO 2009/133059 | 11/2009 |
| WO | WO 2010/037109 | 4/2010 |
| WO | WO 2011/131552 | 10/2011 |
| WO | WO 2012/110987 | 8/2012 |
| WO | WO 2012/150051 | 11/2012 |
| WO | WO 2013/041300 | 3/2013 |
| WO | WO 2013/050230 | 4/2013 |
| WO | WO 2013/050242 | 4/2013 |
| WO | WO 2013/072147 | 5/2013 |
| WO | WO 2015/000637 | 1/2015 |
| WO | WO 2017/005538 | 1/2017 |

OTHER PUBLICATIONS

De Lucas, et al., "Vapor Pressures, Densities, and Viscosities of the (Water + Lithium Bromide + Lithium Formate) System and (Water + Lithium Bromide + Potassium Formate) System," *Journal of Chemical and Engineering Data, American Chemical Society, US* 48(1):18-22 (Jan. 2003).

De Lucas, et al., "Absorption of Water Vapor into Working Fluids for Absorption Refrigeration Systems," *Industrial & Engineering Chemistry Research, American Chemical Society, US* 46(1):345-350 (2007); (published online Dec. 2006).

Domanska, et al., Solubility of 1-Alkyl-3-ethylimidazolium-Based Ionic Liquids in Water and 1-Octanol, *J. Chem. Eng. Data* 53:1126-1132 (Apr. 2008).

Galán, et al., "Solvent Properties of Functionalized Ionic Liquids for $CO_2$ Absorption," *IChemE* 85(A1):31-39 (Jan. 2007).

Glebov, et al., "Experimental Study of Heat Transfer Additive Influence on the Absorption Chiller Performance," *International Journal of Refrigeration* 25:538-545 (Aug. 2002).

Kim, et al., "Surface tension and viscosity of 1-butyl-3-methylimidazolium iodide and 1-butyl-3-methylimidazolium tetrafluoroborate, and solubility of lithium bromide+1-butyl-3-methylimidazolium bromide in water," *Korean J. Chem. Eng.* 23(1):113-116 (Jan. 2006).

Kim, et al., "Performance Evaluation of Absorption Chiller Using $LiBr + H_2N(CH_2)_2OH + H_2O$, $LiBr + HO(CH_2)_3OH + H_2O$, and $LiBr + (HOCH_2CH_2NH + H_2O$ as Working Fluids," *Applied Thermal Engineering* 19:217-225 (Feb. 1999).

Kim, et al., "Refractive Index and Heat Capacity of 1-Butyl-3-Methylimidazolium Bromide and 1-Butyl-3-Methylimidazolium Tetrafluoroborate, and Vapor Pressure of Binary Systems for 1-Butyl-3-Methylimidazolium Tetrafluoroborate—Trifluoroethanol," *Fluid Phase Equilibria* 218:215-220 (Apr. 2004).

Li, et al., "Correlation and Prediction of the Solubility of $CO_2$ and $H_2S$ in an Aqueous Solution of 2-Piperidineethanol and Sulfolane," *Ind. Eng. Chem. Res.* 37:3098-3104 (May 1998).

Liu, et al., The physical properties of aqueous solution of room-temperature ionic liquids based on imidazolium:Database and Evaluation, *J. Mol. Liquids* 140:68-72 (Jan. 2008).

Mitsubishi Heavy Industries, Ltd., "Flue Gas $CO_2$ Recovery Technology and Its Application to EOR: an Effective Strategy for Addressing the Issues of Global Warming and Peaking Oil Supply," vol. 44, p. 20-23 (2007).

Perez-Blanco, "A Model of an Ammonia-Water Falling Film Absorber," ASHRAE Transactions vol. 94, pp. 467-483, 1988; Presented at the winter meeting in Dallas Texas of the American Society of Heating, Refrigerating and Air-Conditioning Engineers, Inc. (1988).

Rolker, et al., "Abtrennung von Kohlendioxid aus Rauchgasen mittels Absorption," *Chemie Ingenieur Technik* 78:416-424; with English language abstract attached (Jul. 2006).

Wasserscheid, et al., "Ionic Liquids—New "Solutions" for Transition Metal Catalysis," *Angew. Chem. Int. Ed.* 39:3772-3789 (Nov. 2000).

Wu, et al., "Novel Ionic Liquid Thermal Storage for Solar Thermal Electric Power Systems," *Proceeding of Solar Forum. Solar Energy: The Power to Choose* (Apr. 21-25, 2001).

Yoon, et al., "Cycle Analysis of Air-Cooled Absorption Chiller Using a New Working Solution," *Energy* 24:795-809 (Sep. 1999).

Zhang, et al., "Screening of ionic Liquids to Capture CO2 by COSMO-RS and Experiments," *AIChE Journal* 54(10):2171-2728 (Oct. 2008).

Zhou, The Vapor Surfactant Theory of Absorption and Condensation Enhancement, *Proc. Int. Sorption Heat Pump Conference*, (Sep. 24-27, 2002).

Ziegler, et al., "Heat-Transfer Enhancement by Additives," *International Journal of Refrigeration* 19:301-309 (Jun. 1996).

Ziegler, et al., "Multi-effect absorption chillers," *Rev. Int. Froid* 16(5):301-311 (1993).

Ziegler, et al., "Recent developments and future prospects of sorption heat pump systems," *Int. J. Therm. Sci.* 38:191-208 (Mar. 1999).

U.S. Appl. No. 14/372,287, filed Jul. 15, 2014, Schraven.

English language translation of Office Action for Chinese application 201280028524.0 (counterpart of copending U.S. Appl. No. 14/124,472) filed in China on May 25, 2012.

"Mutual Solubility of Water and Pyridine Derivatives" by Richard M. Stephenson, *J. Chem. Eng. Data* 38, p. 428-431, (Jul. 1993).

"Review of Organic Functional Groups: Introduction to Medicinal Organic Chemistry" by Thomas L. Lemke, Lippincott Williams & Wilkins, p. 40 (2003).

"Review of Organic Functional Groups: Introduction to Medicinal Organic Chemistry" by Thomas L. Lemke, Lippincott Williams & Wilkins, p. 39 (2003).

U.S. Appl. No. 14/399,139, filed Nov. 5, 2014, Willy.

Encylopedia of Chemical Process and Design, Ed. John J. McKetta, vol. 32. Marcel Deckker, Inc. (1990) pp. 123-126.

Blachly, et al., "Stabilization of Monoethanolmine Solutions in Carbon Dioxide Scrubbers," *J. Chem. Eng. Data* 11(3):401-403 (Jul. 1966).

Call, "Aminoxyle—eine Klasse stabiler," *Pharmazie in unserer Zeit* 3:83-95 (Jan. 1977); with English language translation attached.

Kirchhoff, et al., "Triacetoneamine Derivatives Industrial Applications and Recent Developments," pp. 1-9, Addcon World '99 (Two-Day Conference, Oct. 1999).

Lewin, et al., "Molecular Features Associated with Polyamine Modulation of NMDA Receptors," *J. Med. Chem.* 41:988-995 (published online Feb. 1998).

Luo, et al., "Dehumidification performance of [EMIM]$BF_4$," *Applied Thermal Engineering* 31(14-15):2772-2777 (Oct. 2011).

Luo, et al., "Investigation of feasibility of ionic liquids used in solar liquid desiccant air conditioning system," *Solar Energy* 86(9):2781-2724 (Sep. 2012).

(56) References Cited

OTHER PUBLICATIONS

Ionische Flüssigkeiten—Polarität und Wechselwirkungen mit silikatischen Oberflächen, Dissertation Technische Universität Chemnitz (Nov. 2011); with English language translation of pp. 14, 24, 39-41, 48-49 and 111; also sections 2.3.3, 3.1.1 and 5.3.
Projekt der Deutschen Bundesstiftung: Gasreinigung mit ionischen Flüssigkeiten Umwelt; Endbericht (Sep. 2009); with English language translation of pp. 18-23 and 90-92.
Satori, et al., "Sterically Hindered Amines for $CO_2$ Removal from Gases," *Ind. Eng. Chem. Fundam.* 22(2):239-249 (accepted Jan. 1983).
Gerald Scott, Develpoments in polymer stabilization-5, Chapter 3: Antioxidant action of sterically hindered amines and related compounds, Shlyapintokh and Ivanor; pp. 41-70, Applied Science Publishers (1982).
Shao & Stangeland, "Amines Used in $CO_2$ Capture—Health and Environmental Impacts," Bellona Report (Sep. 2009).
Ulmann's Encyclopedia of Industrial Chemistry, 5th Edition, vol. 83, "Antioxidants" pp. 91-104 (1985).
Wellner, et al., "Entwässerung ionischer Flüssigkeiten in einem Fallfilmverdampfer," *Chemie Ingenieur Technik* 83(9):1493-1501(Jul. 2011); with complete English language translation.
Yunus, "Gaslöslichkeit in ionischen Flüssigkeiten," IsoSORP Application Note Nr. 4:1-2 (Feb. 2014); with complete English language translation.
Office Action for copending U.S. Appl. No. 14/372,287, mailed Jun. 22, 2016.
Kanakubo, et al., "CO2 solubility in and physical properties for ionic liquid mixtures of 1-butyl-3-methylimidazolium acetate and 1-butyl-3-methylimidazolium bis(trifluoromethanesulfonyDamide," Journal ofMolecular Liquids 217:112-119 (2016); available online Feb. 12, 2016.
Krannich, et al., "Characterization of Six Hygroscopic Ionic Liquids with Regard to Their Suitability for Gas Dehydration: Density, Viscosity, Thermal and Oxidative Stability, Vapor Pressure, Diffusion Coefficient, and Activity Coefficient of Water," Journal of Chemical Engineering & Data 61:1162-1176 (Feb. 2016).
Kriebel, et al., "Absorption, 2. Design of Systems and Equipment," Ulmann's Encyclopedia of Industrial Chemistry, vol. 1, pp. 75-90 (2008).
Lall-Ramnarine, et al., "Probing the Physical Properties, Synthesis and Cellulose Dissolution Ability of Dialkyl Phosphate Ionic Liquids," Phosphorous, Sulfur, and Silicon 190:891-895 (2015).
Lungwitz, Ralf, "Ionische Fliissigkeiten - Polaritat and Wechselwirkungen mit silikatischen Oberflachen," Dissertation Technische Universitat Chemnitz (Nov. 2011); with English language translation of relevant parts.
English language translation of Mao, et al., "Development and Application of New Technique for Recovery of Low Partial Pressure Carbon Dioxide," Journal of Chemical Industry & Engineering 25(3):12-15 (Jun. 2004).
English language translation of Rolker, et al., "Separation of carbon dioxide from flue gases by means of absorption," Chemie Ingenieur Tecknik 78(4):416-424 (Jul. 2006).
Oecd Guidelines for the Testing of Chemicals, Test No. 104, items 14-19, (adopted May 1981).
Projekt der Deutschen Bundesstiftung: Gasreinigung mit ionischen Fliissig,keiten Umwelt; Endbericht (Sep. 2009); with English language translation of relavant parts.
English language translation of Xiao, "Study on Technique for Recovery of Carbon Dioxide from Flue Gas," Modern Chemical Industry 24(5):47-49 (May 2004).
U.S. Appl. No. 15/619,561, filing date Jun. 12, 2017, Irfan.
U.S. Appl. No. 15/619,566, filing date Jun. 12, 2017, Willy.
U.S. Appl. No. 15/619,567, filing date Jun. 12, 2017, Wang.
U.S. Appl. No. 15/619,573, filing date Jun. 12, 2017, Zehnacker.
U.S. Appl. No. 15/619,577, filing date Jun. 12, 2017, Zehnacker.
U.S. Appl. No. 15/619,584, filing date Jun. 12, 2017, Zehnacker.
English language machine translation of Chinese patent reference CN 10233554-5 which was cited in a Supplemental IDS submitted date Oct. 4, 2016 as document B3.
English language translation of German patent reference DD 266 799 which was cited in an IDS submitted date Sep. 26, 2014 as document B1.
English language machine translation of German patent reference DE 36 23 680 which was cited in an IDS submitted date Sep. 26, 2014 as document B4.
English language machine translation of German patent reference DE 195 11 709 which was cited in an IDS submitted date Sep. 26, 2014 as document B5.
English language machine translation of German patent reference DE 103 33 546 which was cited in an IDS submitted date Sep. 26, 2014 as document B6.
English language machine translation of German patent reference DE 10 2004 053 167 which was cited in an IDS submitted date Sep. 26, 2014 as document B7.
English language machine translation of German patent reference DE 10 2010 004 779 which was cited in a Supplemental IDS submitted date Oct. 4, 2016 as document B5.
English language machine translation of German patent reference DE 10 2011 055 859 which was cited in a Supplemental IDS submitted date Oct. 4, 2016 as document B6.
English language machine translation of European patent reference EP 0 033 529 which was cited in an IDS submitted date Sep. 26, 2014 as document B8.
English language translation of European patent reference EP 2 636 715 which was cited in a Supplemental IDS submitted date Oct. 4, 2016 as document B9.
English language machine translation of French patent reference FR 2 900 841 which was cited in an IDS submitted date Sep. 26, 2014 as document B12.
English language machine translation of Japanese patent reference JP 61-129019 which was cited in an IDS submitted date Sep. 26, 2014 as document B14.
English language machine translation of Japanese patent reference JP 1-134180 which was cited in an IDS submitted date Sep. 26, 2014 as document B16.
English language machine translation of Japanese patent reference JP 2-298767 which was cited in an IDS submitted date Sep. 26, 2014 as document B17.
English language machine translation of Japanese patent reference JP-4-268176 which was cited in an IDS submitted date Sep. 26, 2014 as document B18.
English language machine translation of Japanese patent reference JP 2001-219164 which was cited in an IDS submitted date Sep. 26, 2014 as document B21.
English language machine translation of Japanese patent reference JP 2004-44945 which was cited in an IDS submitted date Sep. 26, 2014 as document B23.
English language machine translation of Russian patent reference RU 2 101 625 which was cited in a Supplemental IDS submitted date Oct. 4, 2016 as document B11.
English language machine translation of Russian patent reference RU 2 183 003 which was cited in a Supplemental IDS submitted date Oct. 4, 2016 as document B12.
English language translation of International patent reference WO 2013/050230 which was cited in an IDS submitted date Sep. 26, 2014 as document B28.
English language translation of International patent reference WO 2013/050242 which was cited in an IDS submitted date Sep. 26, 2014 as document B29.
U.S. Appl. No. 15/486,300, filing date Apr. 13, 2017, Bahlmann.

METHOD AND ABSORPTION MEDIUM FOR ABSORBING CO₂ FROM A GAS MIXTURE

CROSS REFERENCE TO RELATED APPLICATIONS

The present application is US national stage of international application PCT/EP2012/073778, which had an international filing date of Nov. 28, 2012. Priority is claimed to German application 10 2012 200 907.8, filed on Jan. 23, 2012.

The invention relates to a process and an absorption medium for absorbing $CO_2$ from a gas mixture.

Numerous industrial and chemical operations give rise to gas streams with an unwanted $CO_2$ content, and the content of $CO_2$ must be reduced for further processing, for transport or in order to avoid $CO_2$ emissions.

On the industrial scale, aqueous potassium carbonate solutions or aqueous solutions of alkanolamines are typically used as absorption media for the absorption of $CO_2$ from a gas mixture. The loaded absorption medium is regenerated by heating, depressurization to a lower pressure, or stripping, with the carbon dioxide being desorbed. After the regenerating operation, the absorption medium can be used again. These techniques are described in, for example, Kohl, A. L.; Nielsen, R. B., "Gas Purification", 5th edn. Gulf Publishing, Houston 1997.

Techniques which use an aqueous solution of an alkanolamine as absorption medium have the disadvantage that the removal of $CO_2$ by absorption and subsequent desorption requires a relatively large amount of energy, and that alkanolamines are volatile, possibly necessitating the removal of alkanolamine from the gas after absorption, in order to reduce the loss of amine and to avoid emission of environmentally hazardous substances.

Techniques which use an aqueous potassium carbonate solution as absorption medium have the disadvantage that the absorption of $CO_2$ into the absorption medium is slow, and that in a cycle of absorption and desorption, the capacity of the absorption medium, referred to as $CO_2$ uptake, is low.

From around 1935, aqueous solutions of potassium N-methylalaninate and potassium N,N-dimethylglycinate were employed for the absorption of $CO_2$ and $H_2S$ from gas streams under the trade names Alkazid M and Alkazid DIK, but are nowadays rarely in industrial use. During $CO_2$ absorption, aqueous solutions of potassium N,N-dimethylglycinate show a too slow uptake of $CO_2$ into the absorption medium. For $CO_2$ absorption, potassium N-methylalaninate has been replaced by alkanolamines, which are easier to prepare.

Laid-open specification DE 2123773 proposes adding an N-alkylamino acid as activator in an amount between 2 and 5 wt % to the aqueous potassium carbonate solution in order to improve the mass transfer of $CO_2$. N-isopropylglycine is mentioned as an N-alkylamino acid suitable for this purpose. U.S. Pat. No. 4,405,586 describes N-sec-butylglycine as a suitable activator for the same purpose. U.S. Pat. No. 4,094,957 alternatively describes a mixture of at least one sterically hindered amine and an amino acid as additive, and U.S. Pat. No. 4,405,579 alternatively describes a mixture of a sterically hindered, monosubstituted alpha-amino acid and a tertiary alpha-amino acid as additive.

The addition of amino acid salts as an activator may improve the absorption rate when using an aqueous potassium carbonate solution, but the disadvantage of a low $CO_2$ uptake remains, resulting in high mass flows of absorption medium and, consequently, a high energy consumption in order to heat the absorption medium when desorbing $CO_2$.

EP 0 079 767 A2 describes the preparation of N-isopropylglycine by reductive amination of acetone with glycine and hydrogen in aqueous solution in the presence of palladium-on-carbon as hydrogenation catalyst.

EP 0 187 130 describes the preparation of N-isopropylglycine by reductive amination of glyoxylic acid with isopropylamine and hydrogen in aqueous solution in the presence of palladium-on-carbon as hydrogenation catalyst.

JP 2002-047258 describes the preparation of N-isopropylglycine by hydrolysis of N-isopropylglycinenitrile with aqueous sodium hydroxide solution to form sodium N-isopropylglycinate, and subsequent neutralization with an acidic ion exchanger.

It has now been found that for an absorption of $CO_2$ from a gas mixture, the use of an absorption medium comprising water and 5 to 50 wt % of amino acid salts of the formula $R^1R^2CHNHCH_2COOK$, where $R^1$ and $R^2$ are n-alkyl radicals together having 2 to 4 carbon atoms, provides a technically more useful combination of high weight-based $CO_2$ absorption capacity in cyclical operation, rapid absorption of $CO_2$ into the absorption medium, and simple and waste-free preparability of the absorption medium, as compared to the known Alkazid M and Alkazid DIK absorption media.

The invention accordingly provides a process for absorbing $CO_2$ from a gas mixture by contacting the gas mixture with an absorption medium which comprises water and 5 to 50 wt % of amino acid salts of formula (I)

$$R^1R^2CHNHCH_2COOK \qquad (I)$$

in which $R^1$ and $R^2$ are n-alkyl radicals, and the radicals $R^1$ and $R^2$ together have 2 to 4 carbon atoms.

Additionally provided by the invention are the absorption medium used in the process of the invention, and also a process for preparing the absorption medium of the invention, with the steps of a) reductively aminating at least one ketone of formula (II)

$$R^1R^2C=O \qquad (II)$$

in which $R^1$ and $R^2$ are n-alkyl radicals, and the radicals $R^1$ and $R^2$ together have 2 to 4 carbon atoms, with glycine and hydrogen in aqueous solution, in the presence of a solid hydrogenation catalyst, to form an N-alkyl glycine, b) removing the hydrogenation catalyst from the mixture obtained in step a), and c) adding potassium hydroxide, potassium carbonate or potassium hydrogen carbonate to the mixture obtained in step b).

In the process of the invention for absorbing $CO_2$, the absorption medium comprises 5 to 50 wt % of amino acid salts of the formula (I), preferably 10 to 48 wt % and more preferably 15 to 45 wt % of amino acid salts of formula (I). With further preference the absorption medium comprises 20 to 45 wt % and more particularly 35 to 45 wt % of amino acid salts of formula (I). Through the use of amino acid salts of formula (I) in these quantity ranges, it is possible to achieve a high $CO_2$ uptake per unit weight, i.e. a high weight-based $CO_2$ absorption capacity in the cyclical operation of absorption and desorption. At the same time, a rapid absorption of $CO_2$ into the absorption medium is achieved as well, and the gas mixture, after the absorption of $CO_2$ into the absorption medium, contains no environmentally hazardous constituents of the absorption medium.

Suitable amino acid salts of formula (I) include potassium N-isopropylglycinate ($R^1$, $R^2$=methyl), potassium N-(sec-butyl)glycinate ($R^1$=ethyl, $R^2$=methyl), potassium N-(2-pentyl)glycinate ($R^1$=n-propyl, $R^2$=methyl) and potassium N-(3-pentyl)glycinate ($R^1$, $R^2$=ethyl), and mixtures of these compounds. The amino acid salts of formula (I) in the absorption medium preferably consist of more than 90 wt % of potassium N-isopropylglycinate. The high solubilities of N-isopropylglycine and potassium N-isopropylglycinate allow the process of the invention to be operated with a high $CO_2$ uptake without precipitation of amino acid or of amino acid salt.

In the process of the invention for absorbing $CO_2$, the absorption medium preferably further comprises potassium carbonate and/or potassium hydrogen carbonate in addition to amino acid salts of formula (I). The potassium carbonate and/or potassium hydrogen carbonate content is preferably selected such that the molar ratio of potassium ions in the form of potassium carbonate or potassium hydrogen carbonate to amino acid salts of formula (I) is in the range from 0.01 to 0.5. More preferably the molar ratio is in the range from 0.01 to 0.1. The presence of potassium carbonate and/or potassium hydrogen carbonate as well as amino acid salts of formula (I) ensures that any nitrogen oxide and/or sulfur dioxide contamination of the gas mixture has no deleterious consequences for the $CO_2$ uptake of the absorption medium, since these impurities, following absorption into the absorption medium, are converted with potassium carbonate and/or potassium hydrogen carbonate into potassium nitrate and potassium sulfate, respectively, and do not lead to any decrease in the amount of amino acid salts of formula (I).

In the process of the invention for absorbing $CO_2$, the absorption medium preferably comprises at least 40 wt % of water. The absorption medium may further comprise one or more physical solvents in addition to water and amino acid salts of formula (I). The fraction of physical solvents in this case may be up to 20 wt %. Suitable physical solvents include sulfolane, aliphatic acid amides, such as N-formylmorpholine, N-acetylmorpholine, N-alkylpyrrolidones, especially N-methyl-2-pyrrolidone, or N-alkylpiperidones, and also diethylene glycol, triethylene glycol and polyethylene glycols and their alkyl ethers, especially diethylene glycol monobutyl ether. Preferably, however, the absorption medium contains no physical solvent.

The absorption medium may additionally comprise additives, such as corrosion inhibitors, wetting-promoting additives and defoamers.

All compounds known to the skilled person as suitable corrosion inhibitors for the absorption of $CO_2$ using alkanolamines can be used as corrosion inhibitors in the absorption medium of the invention, in particular the corrosion inhibitors described in U.S. Pat. No. 4,714,597.

The cationic surfactants, zwitterionic surfactants and nonionic surfactants known from WO 2010/089257 page 11, line 18 to page 13, line 7 are preferably used as wetting-promoting additive.

All compounds known to the skilled person as suitable defoamers for the absorption of $CO_2$ using alkanolamines can be used as defoamers in the absorption medium.

In the process of the invention for absorbing $CO_2$, the gas mixture may be a natural gas, a methane-containing biogas from a fermentation, composting or a sewage treatment plant, a combustion off-gas, an off-gas from a calcination reaction, such as the burning of lime or the production of cement, a residual gas from a blast-furnace operation for producing iron, or a gas mixture resulting from a chemical reaction, such as, for example, a synthesis gas containing carbon monoxide and hydrogen, or a reaction gas from a steam-reforming hydrogen production process. The gas mixture is preferably a combustion off-gas, a natural gas or a biogas, more preferably a combustion off-gas, for example from a power plant.

The gas mixture can contain further acid gases, for example COS, $H_2S$, $CH_3SH$ or $SO_2$, in addition to $CO_2$. In a preferred embodiment, the gas mixture contains $H_2S$ in addition to $CO_2$. In another preferred embodiment, the gas mixture comprises nitrogen oxides and/or $SO_2$ in addition to $CO_2$. A combustion off-gas is preferably desulfurized beforehand, i.e. the $SO_2$ content of the gas mixture is depleted using a desulfurization process known from the prior art, preferably by means of gas scrubbing with milk of lime, before the absorption process of the invention is carried out.

Before being brought into contact with the absorption medium, the gas mixture preferably has a $CO_2$ content in the range from 0.1 to 50% by volume, particularly preferably in the range from 1 to 20% by volume, and most preferably in the range from 8 to 20% by volume.

The gas mixture can contain oxygen, preferably in a proportion of from 0.1 to 25% by volume and particularly preferably in a proportion of from 0.1 to 10% by volume, in addition to $CO_2$.

For the process of the invention for absorbing $CO_2$, all apparatus suitable for contacting a gas phase with a liquid phase can be used to contact the gas mixture with the absorption medium. Preferably, absorption columns or gas scrubbers known from the prior art are used, for example membrane contactors, radial flow scrubbers, jet scrubbers, venturi scrubbers, rotary spray scrubbers, random packing columns, ordered packing columns or tray columns. With particular preference, absorption columns are used in countercurrent flow mode.

In the process of the invention for absorbing $CO_2$, the absorption is carried out preferably at a temperature of the absorption medium in the range from 0 to 80° C., more preferably 20 to 70° C. When using an absorption column in countercurrent flow mode, the temperature of the absorption medium is more preferably 30 to 60° C. on entry into the column, and 35 to 70° C. on exit from the column.

The $CO_2$-containing gas mixture is preferably contacted with the absorption medium at an initial partial pressure of $CO_2$ of 0.01 to 4 bar. More preferably the initial partial pressure of $CO_2$ in the gas mixture is from 0.05 to 3 bar. The total pressure of the gas mixture is situated preferably in the range from 0.8 to 50 bar, more preferably 0.9 to 30 bar.

In a preferred embodiment of the process of the invention for absorbing $CO_2$, $CO_2$ absorbed in the absorption medium is desorbed again by increasing the temperature and/or reducing the pressure and the absorption medium after this desorption of $CO_2$ is used again for absorbing $CO_2$. The desorption is preferably carried out by increasing the temperature. By such cyclic operation of absorption and desorption, $CO_2$ can be entirely or partially separated from the gas mixture and obtained separately from other components of the gas mixture.

As an alternative to the increase in temperature or the reduction in pressure, or in addition to an increase in temperature and/or a reduction in pressure, it is also possible to carry out a desorption by stripping the absorption medium loaded with $CO_2$ by means of an inert gas, such as air or nitrogen.

If, in the desorption of $CO_2$, water is also removed from the absorption medium, water may be added as necessary to the absorption medium before reuse for absorption.

All apparatus known from the prior art for desorbing a gas from a liquid can be used for the desorption. The desorption is preferably carried out in a desorption column. Alternatively, the desorption of $CO_2$ may also be carried out in one or more flash evaporation stages.

The desorption is carried out preferably at a temperature in the range from 50 to 200° C. In a desorption by an increase in temperature, the desorption of $CO_2$ is carried out preferably at a temperature of the absorption medium in the range from 50 to 180° C., more preferably 80 to 150° C. The temperature during desorption is then preferably at least 20° C., more preferably at least 30° C., above the temperature during absorption. In a desorption by an increase in temperature, preferably a stripping is carried out with steam, which is generated by evaporating a portion of the absorption medium.

In a desorption by reducing the pressure, the desorption is carried out preferably at a pressure in the range from 0.01 to 10 bar.

In a preferred embodiment of the process of the invention for absorbing $CO_2$, the desorption is carried out by stripping with an inert gas such as air or nitrogen in a desorption column. The stripping in the desorption column is preferably carried out at a temperature of the absorption medium in the range from 60 to 100° C. Stripping enables a low residual content of $CO_2$ in the absorption medium to be achieved after desorption with a low energy consumption.

In a particularly preferred embodiment of the process of the invention for absorbing $CO_2$, the steps of absorption and desorption are repeated several times. The absorption medium further comprises potassium carbonate and/or potassium hydrogen carbonate, and the molar ratio of potassium ions in the form of potassium carbonate or potassium hydrogen carbonate to amino acid salts of formula (I) is maintained in the range from 0.01 to 0.5 by addition of potassium hydroxide, potassium carbonate or potassium hydrogen carbonate. The molar ratio is preferably maintained in the range from 0.01 to 0.5, more preferably in the range from 0.01 to 0.1, by addition of potassium hydroxide. By such addition of potassium hydroxide, potassium carbonate or potassium hydrogen carbonate, it is possible to prevent a decrease in the $CO_2$ uptake of the absorption medium, even over a long period of cyclical operation, during an absorption of $CO_2$ from gas mixtures which include nitrogen oxides and/or sulphur dioxide as impurities.

The absorption medium of the invention for absorbing $CO_2$ from a gas mixture comprises water and 5 to 50 wt % of amino acid salts of formula

$$R^1R^2CHNHCH_2COOK \qquad (I)$$

in which $R^1$ and $R^2$ are n-alkyl radicals, and the radicals $R^1$ and $R^2$ together have 2 to 4 carbon atoms. The absorption medium of the invention preferably has a composition as described above for the absorption medium in preferred embodiments of the process of the invention for absorbing $CO_2$.

The process of the invention for preparing an absorption medium comprises a first step a) of reductively aminating at least one ketone of formula $R^1R^2C=O$, in which $R^1$ and $R^2$ are n-alkyl radicals, and the radicals $R^1$ and $R^2$ together have 2 to 4 carbon atoms, with glycine and hydrogen. Suitable ketones of formula $R^1R^2C=O$ are acetone, 2-butanone, 2-pentanone and 3-pentanone, and mixtures of these compounds. A ketone of formula $R^1R^2C=O$ employed with preference is acetone. The reductive amination takes place in aqueous solution in the presence of a solid hydrogenation catalyst. The product of the reductive amination is at least one N-alkylglycine of formula $R^1R^2CHNHCH_2COOH$. With acetone as the ketone of formula $R^2R^2C=O$, the product of the reductive amination is N-isopropylglycine.

The reductive amination is preferably carried out in an aqueous solution which comprises no other organic solvent further to glycine and ketones of formula $R^1R^2C=O$.

All heterogeneous catalysts the skilled person knows to be suitable for the reductive amination of ketones can be used as the solid hydrogenation catalyst. Preference is given to using a solid hydrogenation catalyst which comprises palladium on a support material, more preferably palladium on activated carbon supports.

The reductive amination is carried out preferably at a temperature of 0 to 150° C., more preferably 40 to 100° C. The hydrogen partial pressure on reductive amination is kept preferably in a range from 1 to 30 bar, more preferably 4 to 15 bar.

In a preferred embodiment of the process of the invention for preparing an absorption medium, the pH of the aqueous solution of glycine and ketones of formula $R^1R^2C=O$ is adjusted to a level in the range from 6 to 10, preferably 8 to 9, in the reductive amination step before hydrogen is added.

The process of the invention for preparing an absorption medium comprises, subsequent to step a), a second step b), in which the hydrogenation catalyst is removed from the mixture obtained in step a). The hydrogenation catalyst can be removed using any technique known to the skilled person for solid/liquid separation, for example by filtration or centrifuging. The hydrogenation catalyst is preferably removed by filtration. The hydrogenation catalyst removed can be re-used in step a) of the process.

Steps a) and b) of the process of the invention for preparing an absorption medium may also be combined with one another in the form of a continuous reaction over a fixed bed catalyst, in which an aqueous solution of glycine and ketones of formula $R^1R^2C=O$ is passed in the presence of hydrogen over a fixed bed which comprises the hydrogenation catalyst in the form of a fixed bed catalyst, with the solid/liquid separation in step b) being accomplished by the liquid reaction mixture departing from the fixed bed.

Subsequent to step b), the process of the invention for preparing an absorption medium comprises a third step c), in which potassium hydroxide, potassium carbonate or potassium hydrogen carbonate is added to the catalyst-free mixture obtained in the second step. Preferably potassium hydroxide is added. Potassium hydroxide, potassium carbonate or potassium hydrogen carbonate is added preferably in a molar excess to the N-alkylglycine obtained in step a), in order to convert all of the N-alkylglycine into the corresponding potassium N-alkylglycinate. With particular preference, potassium hydroxide, potassium carbonate or potassium hydrogen carbonate is added until the molar ratio of potassium ions in the form of potassium hydroxide, potassium carbonate or potassium hydrogen carbonate to amino acid salts of formula (I) is in the range from 0.01 to 0.5.

Subsequent to step b) or step c), optionally, water may be removed from the resulting aqueous solution, preferably by distillation, in order to adjust the concentration of amino acid salts of formula (I) in the solution obtained in step c) as desired for its use as an absorption medium in the process of the invention for absorbing $CO_2$. In this case, unreacted ketones of formula $R^1R^2C=O$ may also be removed together with water.

With the process of the invention for preparing the absorption medium, an absorption medium of the invention can be prepared in a simple way from starting materials accessible readily and in large quantities. The process can be carried out without purification steps and virtually without formation of wastes, and requires only a few devices. The solution obtained in step c) can be used without further purification as an absorption medium in the process of the invention for absorbing $CO_2$.

The examples which follow illustrate the invention, though without limiting the subject matter of the invention.

EXAMPLES

Example 1

Preparation of an Aqueous Solution of Potassium N-isopropylglycinate 37.52 g of glycine were dissolved in a mixture of 500 ml of water and 147 ml of acetone. The pH of the solution was then adjusted to a value of 8.5 by addition of 1.49 g of 85 wt % potassium hydroxide. Following addition of 10 g of 5 wt % palladium on activated carbon (50 wt % water-moist), hydrogen was injected to 6 bar, and the mixture was stirred at 55° C. for 14 hours under a constant hydrogen pressure of 6 bar. The catalyst was subsequently removed by vacuum filtration. A $^1$H NMR spectrum of the resulting solution showed N-isopropylglycine and N,N-diisopropylglycine as reaction products of glycine, in a molar ratio of 50:1. The solution was concentrated on a rotary evaporator to approximately 100 ml. Then 31.6 g of 85 wt % potassium hydroxide were added, and the mixture was made up to 222 g with water.

Example 2

Preparation of an Aqueous Solution of Potassium N-(sec-butyl)glycinate 75.1 g of glycine were dissolved in 450 ml of water, and the pH of the solution was adjusted to a value of 8.5 by addition of 3.3 g of 85 wt % potassium hydroxide. Following addition of 108.2 g of 2-butanone and 7.5 g of 5 wt % palladium on activated carbon (50 wt % water-moist), hydrogen was injected to 5 bar, and the mixture was stirred at 55° C. for 48 hours under a constant hydrogen pressure of 5 bar. The catalyst was then removed by vacuum filtration. A $^1$H NMR spectrum of the resulting solution showed N-sec-butylylglycine as reaction product of glycine, and unreacted glycine, in a molar ratio of 50:1. The solution was concentrated on a rotary evaporator to approximately 200 ml. Then 60 g of 85 wt % potassium hydroxide were added, and the mixture was made up to 500 g with water.

Examples 3 to 17

Determination of the $CO_2$ Absorption Capacity

To determine the $CO_2$ loading and the $CO_2$ uptake, 150 g of aqueous absorption medium, containing the proportions of amino acid and potassium hydroxide indicated in table 1, were charged to a thermostatable container with a top-mounted reflux condenser cooled at 3° C. After heating to 40° C. or 100° C., a gas mixture of 14% $CO_2$, 80% nitrogen and 6% oxygen by volume was passed at a flow rate of 59 l/h through the absorption medium, via a frit at the bottom of the container, and the $CO_2$ concentration in the gas stream exiting the reflux condenser was determined by IR absorption using a $CO_2$ analyser. The difference between the $CO_2$ content in the gas stream introduced and in the exiting gas stream was integrated to give the amount of $CO_2$ taken up, and the equilibrium $CO_2$ loading of the absorption medium was calculated. The $CO_2$ uptake was calculated as the difference in the amounts of $CO_2$ taken up at 40° C. and at 100° C. The equilibrium loadings determined in this way at 40° C. and 100° C., in mol $CO_2$/kg absorption medium, and the $CO_2$ uptake in mol $CO_2$/kg absorption medium are given in Table 1.

TABLE 1

| Example | Amino acid | KOH | Loading at 40° C. in mol/kg | Loading at 100° C. in mol/kg | $CO_2$ uptake in mol/kg |
|---|---|---|---|---|---|
| 3* | 30.0 g glycine | 26.5 g | 1.74 | 1.33 | 0.41 |
| 4* | 30.0 g N-methylglycine | 22.5 g | 1.74 | 1.16 | 0.58 |
| 5* | 30.0 g ethylglycine | 19.5 g | 1.92 | 1.08 | 0.84 |
| 6* | 30.0 g N,N-dimethylglycine | 19.5 g | 1.78 | 0.67 | 1.11 |
| 7* | 30.0 g N-propylglycine | 17.1 g | 1.54 | 0.93 | 0.61 |
| 8 | 30.0 g N-isopropylglycine | 17.1 g | 1.81 | 0.82 | 0.99 |
| 9 | 30.0 g N-(sec-butyl) glycine | 14.3 g | 1.44 | 0.63 | 0.81 |
| 10 | 30.0 g N-(3-pentyl) glycine | 13.6 g | 1.32 | 0.54 | 0.78 |
| 11 | 37.6 g N-isopropylglycine | 21.4 g | 2.16 | 0.84 | 1.32 |
| 12* | 45.0 g glycine | 33.4 g | 2.91 | 2.23 | 0.68 |
| 13* | 45.0 g N-methylglycine | 33.5 g | 2.43 | 1.65 | 0.78 |
| 14* | 45.0 g N-methylalanine | 30.0 g | 2.71 | 1.51 | 1.20 |
| 15* | none | 25.7 g | 2.57 | 2.18 | 0.39 |
| 16* | 7.5 g N-methylalanine | 25.7 g | 2.55 | 1.87 | 0.68 |
| 17* | 45.0 g N-methylalanine | 25.7 g | 2.47 | 1.33 | 1.14 |

*not according to the invention

The invention claimed is:

1. An absorption medium for absorbing $CO_2$ from a gas mixture, comprising water and 5 to 50 wt % of amino acid salts of formula (I):

$$R^1R^2CHNHCH_2COOK \qquad (I)$$

in which $R^1$ and $R^2$ are n-alkyl radicals, and the radicals $R^1$ and $R^2$ together have 2 to 4 carbon atoms;
which further comprises potassium ions in the form of potassium carbonate or potassium hydrogen carbonate, wherein the molar ratio of potassium ions in the form of potassium carbonate or potassium hydrogen carbonate to amino acid salts of formula I is in the range from 0.01 to 0.1;
and wherein: more than 90 wt % of the amino acid salts of formula (I) are potassium N-isopropylglycinate.

2. The absorption medium of claim 1, further comprising a corrosion inhibitor, a wetting promoter and/or a defoamer.

3. The absorption medium of claim 1, comprising 10 to 48 wt % of amino acid salts of formula (I).

4. The absorption medium of claim 1, comprising 35 to 45 wt % of amino acid salts of formula (I).

5. The absorption medium of claim 1, comprising more than 40 wt % of water.

6. A process for absorbing $CO_2$ from a gas mixture by contacting the gas mixture with the absorption medium of claim 1.

7. The process of claim 6, wherein the absorption medium comprises 10 to 48 wt % of amino acid salts of formula (I).

8. The process of claim 6, wherein the absorption medium comprises 35 to 45 wt % of amino acid salts of formula (I).

9. The process of claim 6, wherein the absorption medium comprises at least 40 wt % of water.

10. The process of claim 6, wherein the gas mixture is a combustion off-gas, a natural gas or a biogas.

11. The process of claim 6, wherein $CO_2$ absorbed in the absorption medium is desorbed again by increasing the temperature, reducing the pressure or both and, after this desorption of $CO_2$, the absorption medium is used again for absorbing $CO_2$.

12. The process of claim 11, wherein the absorption is carried out at a temperature in the range from 0 to 80° C. and the desorption is carried out at a higher temperature in the range from 50 to 200° C.

13. The process of claim 11, wherein the absorption is carried out at a pressure in the range from 0.8 to 50 bar and the desorption is carried out at a lower pressure in the range from 0.01 to 10 bar.

14. The process of claim 12, wherein the absorption is carried out at a temperature in the range from 20 to 70° C. and the desorption is carried out at a higher temperature in the range from 80 to 150° C.

15. The process of claim 12, wherein desorption is at a temperature at least 30° C. above the temperature during desorption.

16. The process of claim 13, wherein the absorption is carried out at a pressure in the range from 0.9 to 30 bar and the desorption is carried out at a lower pressure in the range from 0.01 to 10 bar.

17. The process of claim 5, wherein the gas mixture further comprises $SO_2$ and, before absorbing $CO_2$ from the gas mixture, the $SO_2$ is depleted using a desulfurization process.

18. The process of claim 6, wherein, before being brought in contact with said absorption medium, the gas mixture has a $CO_2$ content of 0.1-50% by volume.

19. The process of claim 6, wherein, before being brought in contact with said absorption medium, the gas mixture has a $CO_2$ content of 8-20% by volume.

* * * * *